United States Patent
Wang et al.

(10) Patent No.: US 8,927,584 B2
(45) Date of Patent: Jan. 6, 2015

(54) SYNTHESIS OF 2-(4-AMINOPHENYL)BENZOTHIAZOLE DERIVATIVES AND USE THEREOF

(71) Applicant: Kaohsiung Medical University, Kaohsiung (TW)

(72) Inventors: Jeh-Jeng Wang, Kaohsiung (TW); Chao-Cheng Liao, Kaohsiung (TW); Wan-Ping Hu, Kaohsiung (TW); Ho-Chuan Shen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 14/057,332

(22) Filed: Oct. 18, 2013

(65) Prior Publication Data

US 2014/0046290 A1 Feb. 13, 2014

Related U.S. Application Data

(62) Division of application No. 13/032,367, filed on Feb. 22, 2011, now Pat. No. 8,592,603.

(51) Int. Cl.
*A61K 31/428* (2006.01)
*A61K 41/00* (2006.01)
*A61N 5/06* (2006.01)
*C07D 277/66* (2006.01)

(52) U.S. Cl.
CPC .......... *A61K 41/0057* (2013.01); *C07D 277/66* (2013.01); *A61N 5/062* (2013.01)
USPC ............................. 514/367; 548/152; 604/501

(58) Field of Classification Search
None
See application file for complete search history.

(56) References Cited

PUBLICATIONS

Hu et al., Bioorganic & Medicinal Chemistry (Apr. 29, 2010), 18(16), pp. 6197-6207.*

* cited by examiner

*Primary Examiner* — Laura L. Stockton
(74) *Attorney, Agent, or Firm* — WPAT, P.C.; Anthony King

(57) ABSTRACT

The present invention provides a photodynamic therapy to a patient having at least one tumor comprising the steps of: administering a compound of formula 6 (wherein $R_1$ and $R_2$ are defined as the above) in a pharmaceutically acceptable carrier to the patient; waiting for a sufficient time to allow the administered compound to be taken up by a target tissue having the at least one tumor; and irradiating a region of the patient containing the target tissue, wherein growth of the tumor is inhibited.

7 Claims, 8 Drawing Sheets

SYNTHESIS OF 2-(4-AMINOPHENYL)BENZOTHIAZOLE DERIVATIVES AND USE THEREOF

CROSS-REFERENCE OF RELATED APPLICATIONS

This application claims priority and is a divisional application of pending U.S. patent application Ser. No. 13/032,367, filed on Feb. 22, 2011. The entirety of the above-mentioned patent application is hereby incorporated by reference herein and made a part of specification.

FIELD OF THE INVENTION

The present invention relates to a method of preparing a compound of 2-(4-aminophenyl)benzothiazoles. The present invention also relates to a method of providing photodynamic therapy to a patient having at least one tumor by administering the compound in a pharmaceutically acceptable carrier to the patient.

BACKGROUND OF THE INVENTION

Nonmelanoma skin cancer (NMSC) is an increasing problem in the world. Basal cell carcinoma (BCC) is the most common type of NMSC, and most frequently occurs in people with fair skin (Marks, R. Cancer 1995, 75, 607). Photodynamic therapy (PDT), a noninvasive treatment and with excellent cosmetic results, is used for the prevention and treatment of BCC cells (Grapengiesser, S.; Ericson, M.; Gudmundsson, F. Clin. Exp. Dermatol. 2002, 27, 493). It employs a combination of a photosensitizing agent and light (Kiesslich, T.; Krammer, B.; Plaetzer, K. Curr. Med. Chem. 2006, 13, 2189). Light activation of a photosensitizer accumulates in the tumor, and in the presence of molecular oxygen, leads to reactive oxygen species (ROS) generation, which ultimately kills the target cells (Dolmans, D. E.; Fukumura, D.; Jain, R. K. Cancer 2003, 3, 380). Nevertheless, reported cure rates vary, and the transdermal penetration levels for both the photosensitizer and its activating light source are listed as limiting factors. These limitations have prompted the research for new photosensitizers.

2-Phenylbenzothiazoles (FIG. 1) represent a novel class of potent and selective antitumor agents (Bradshaw, T. D.; Wrigley, S.; Shi, D-F.; Schultz, R. J.; Paull, K. D.; Stevens, M. F. G. Br. J. Cancer 1998, 77, 745). For instance, 2-(4-aminophenyl) benzothiazoles (Formula 6, Scheme 1) were originally prepared as synthetic intermediates within a programme to design potential tyrosine kinase inhibitors modeled on structural comparisons with the flavone quercetin and the isoflavone genistein, which compete at the ATP-binding sites of tyrosine kinases (Stevens, M. F. G.; McCall, C. J.; Lelieveld, P.; Alexander, P.; Richter, A.; Davies, D. E. J. Med. Chem. 1994, 37, 1689). However, other biological profiles may also be involved in this complicated biological phenomenon and further investigation is needed to address this issue.

Mitochondria are well known to participate actively in the production of ROS which might be harmful if produced excessively, and are critically involved in the regulation of cell death pathways (Gogvadze; Zhivotovsky, B. J. Bioenerg. Biomembr. 2007, 39, 23). Permeabilization of the mitochondrial outer membrane and subsequent release of proapoptotic proteins from the intermembrane space are viewed as decisive events in the initiation and/or execution of apoptosis (Crompton, M. Biochem. J. 1999, 341, 233). In addition, recent evidence has indicated that ROS play a pivotal role in UVA-induced cell damage (Valencia, A.; Kochevar, I. E. Free Radic. Biol. Med. 2006, 40, 641). Consequently, cell death induced by UVA-activated Formula 6 might be correlated with mitochondrial depolarization. The mitogen-activated protein kinase (MAPK) family consists of extracellular signal-regulated kinase (ERK), c-Jun N-terminal kinase (JNK), and p38 MAPK. JNK and p38 MAPK pathways are known to be activated by a variety of environmental stresses and chemicals (Roulston, A.; Reinhard, C.; Amiri, P.; Williams, L. T. J. Biol. Chem. 1998, 273, 10232), while the ERK cascade is activated by mitogenic stimuli and is critical for proliferation and survival (Nagata, Y.; Todokoro, K. Blood 1999, 94, 853). However, ERK signaling has been suggested to be proapoptotic in cells undergoing apoptosis (Xiao, D.; Singh, S. V. Cancer Res. 2002, 62, 3615).

SUMMARY OF THE INVENTION

Figure 1:
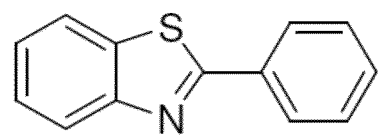
FIG. 1 shows the structures of 2-phenyl-benzothiazoles.

The present invention relates to a method of preparing a compound of formula 6

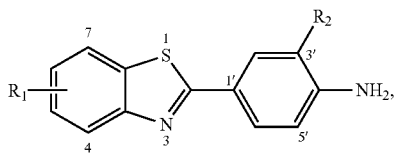

comprising:
(a) reacting a compound of formula 1

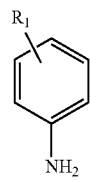

with a compound of formula 2

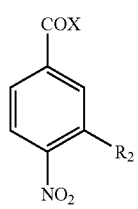

to form a compound of formula 3

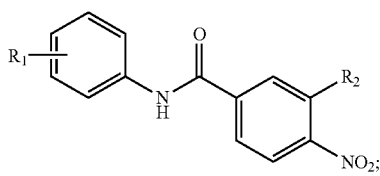

wherein X of formula 2 is Cl or OH;
(b) treating the compound formula 3 with Lawesson's reagent to form a compound of formula 4

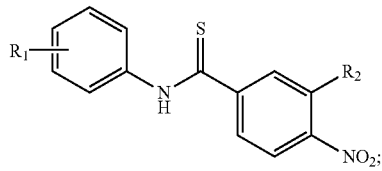

(c) reacting a compound of formula 4 with potassium ferricyanide to produce a compound of formula 5

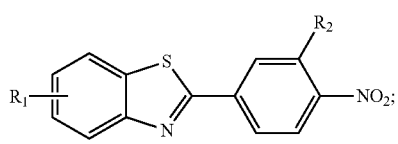

and
(d) performing catalytic reduction of nitro group of the compound of formula 5 with palladium on charcoal to generate the compound of formula 6,
wherein $R_1$ of formulae 1-6 is H, $C_{1-10}$ alkyl, $C_{1-10}$ alkoxy or $C_{1-10}$ haloalkyl, and $R_2$ of formulae 1-6 is H or $C_{1-10}$ alkyl.

The present invention relates to a method of providing photodynamic therapy to a patient having at least one tumor comprising the steps of: administering a compound of formula 6 (wherein $R_1$ and $R_2$ are defined as the above) in a pharmaceutically acceptable carrier to the patient; waiting for a sufficient time to allow the administered compound to be taken up by a target tissue having the at least one tumor; and irradiating a region of the patient containing the target tissue, wherein growth of the tumor is inhibited.

DETAILED DESCRIPTION OF THE INVENTION

In this invention, the Applicant initiated experiments aimed at characterizing the above signaling molecules in the process of apoptosis after BCC cells were treated with 6-UVA.

The aim of this invention was to evaluate the newly synthesized Formula 6 as photosensitizing agents and investigate the apoptotic mechanisms induced by 6-UVA on BCC cells.

The synthesis and biological evaluation of compounds of Formula 6 (2-(4-aminophenyl)benzothiazole derivatives) as photosensitizing agents was carried out in the present invention. Only 4 steps are required for synthesis of compounds of Formula 6, and the materials required for the synthesis are very cheap. Therefore, a large scale synthesis of compounds of Formula 6 can be achieved by the present invention. Due to these compounds having chromophoric structure and light absorption in the UVA range (320-400 nm), the in vitro study analyses the photosensitive effect of UVA-activated Formula 6 in BCC cells. One can speculate that UVA will produce side effects such as carcinogenesis and photoaging, but in the system of the present invention, these do not appear because the exposure time required for Formula 6 activation was very short and did not lead to chronic exposure to UVA.

The terms used in the description herein will have their ordinary and common meaning as understood by those skilled in the art, unless specifically defined otherwise. As used throughout the instant application, the following terms shall have the following meanings:

The term "UVA" refers to ultraviolet radiation of relatively long wavelengths.

The term "6-UVA" refers to UVA-activated compound of Formula 6.

The term "6f-UVA" refers to UVA-activated compound of Formula 6f.

Therefore, the present invention provides a method of preparing a compound of formula 6

6

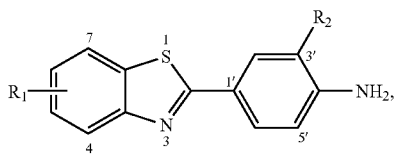

comprising:

(a) reacting a compound of formula 1

1

with a compound of formula 2

2

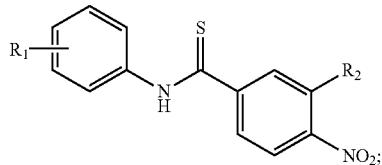

to form a compound of formula 3

3

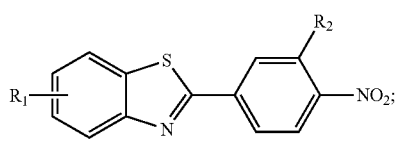

wherein X of formula 2 is Cl or OH;

(b) treating the compound formula 3 with Lawesson's reagent to form a compound of formula 4

4

(c) reacting a compound of formula 4 with potassium ferricyanide to produce a compound of formula 5

5 and (d) performing catalytic reduction of nitro group of the compound of formula 5 with palladium on charcoal to generate the compound of formula 6, wherein $R_1$ of formulae 1-6 is H, $C_{1-10}$ alkyl, $C_{1-10}$ alkoxy or $C_{1-10}$ haloalkyl, and $R_2$ of formulae 1-6 is H or $C_{1-10}$ alkyl.

In a preferred embodiment, $R_1$ of formulae 1-6 is H, 6-Et, 6-OMe, 6-OCH$_3$, 6-Me, 7-OMe or 6-CF$_3$, and $R_2$ of formulae 1-6 is H or CH$_3$. More preferably, $R_1$ of formulae 1-6 is H, 6-Et, 6-OMe, 6-Me, 7-OMe or 6-CF$_3$ when $R_2$ of formulae 1-6 is H; $R_1$ of formulae 1-6 is H, 6-OCH$_3$, 6-Et or 6-CF$_3$ when $R_2$ of formulae 1-6 is CH$_3$. Most preferably, $R_1$ of formulae 1-6 is 6-CF$_3$, and $R_2$ of formulae 1-6 is H.

The present invention also provides a method of providing photodynamic therapy to a patient having at least one tumor comprising the steps of: administering the compound of formula 6 (wherein $R_1$ is H, $C_{1-10}$ alkyl, $C_{1-10}$ alkoxy or $C_{1-10}$ haloalkyl, and $R_2$ is H or $C_{1-10}$ alkyl; preferably, $R_1$ is H, 6-Et, 6-OMe, 6-OCH$_3$, 6-Me, 7-OMe or 6-CF$_3$, and $R_2$ is H or CH$_3$; more preferably, $R_1$ of formulae 1-6 is H, 6-Et, 6-OMe, 6-Me, 7-OMe or 6-CF$_3$ when $R_2$ of formulae 1-6 is H; $R_1$ of formulae 1-6 is H, 6-OCH$_3$, 6-Et or 6-CF$_3$ when $R_2$ of formulae 1-6 is CH$_3$, most preferably, $R_1$ of formulae 1-6 is 6-CF$_3$, and $R_2$ of formulae 1-6 is H) in a pharmaceutically acceptable carrier to the patient; waiting for a sufficient time to allow the administered compound to be taken up by a target tissue having the at least one tumor; and irradiating a region of the patient containing the target tissue, wherein growth of the tumor is inhibited.

In a preferred embodiment, the patient is having a skin cancer. More preferably, the patient is having a basal cell carcinoma.

In a preferred embodiment, the compound of formula 6 is activated by UVA. Preferably, the growth of the tumor is inhibited by apoptosis of tumor cells. More preferably, intracellular H$_2$O$_2$ levels in the tumor cells are increased, and intracellular mitochondrial membrane potential ($\Delta\Psi_{mt}$) in the tumor cells is declined.

EXAMPLES

The examples below are non-limiting and are merely representative of various aspects and features of the present invention.

Example 1

Methods and Materials

Synthesis

Figure 2:
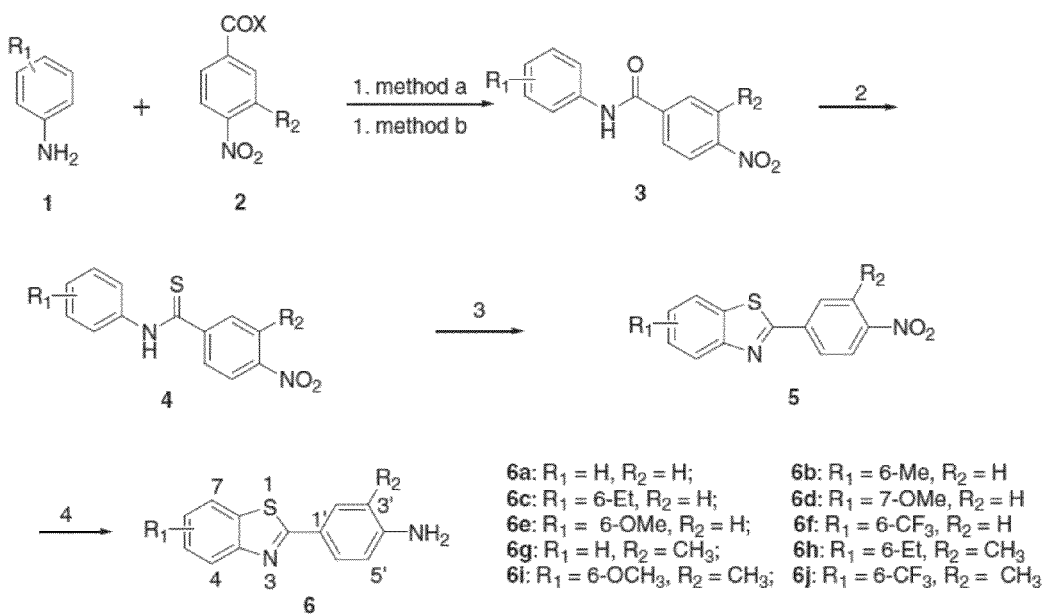
FIG. 2 shows total synthesis of 2-(4-aminophenyl)benzothiazoles (Formula 6). Reagents and conditions: (1) method a: X=Cl, pyridine, reflux; method b: X=OH, $SOCl_2$, benzene, reflux. (2) Lawesson's reagent, chlorobenzene, 135° C. (3) $K_3Fe(CN)_6$ aq, NaOH, 90° C. (4) $H_2$/Pd/C 10%, $CH_2Cl_2$, 25° C.

The preparation of 2-(4-aminophenyl)benzothiazoles (Formula 6) was shown in FIG. 2. 4-Nitro-N-phenyl benzamides (Formula 3) were obtained by the reaction of anilines (Formula 1) with nitrobenzoyl chlorides (Formula 2) in pyridine under reflux for 4 h (method A). Alternatively, anilines (Formula 1) were coupled to nitrobenzoic acids (Formula 2) in the presence of thionyl chloride in benzene under reflux condition to give benzamides (Formula 3) in high yields (method B). The benzamides (Formula 3) were treated with Lawesson's reagent in chlorobenzene under reflux to form 4-nitro-N-phenylthiobenzamides (Formula 4) in good yields. Cyclization of Formula 4 promoted by potassium ferricyanide to produce 2-(4-nitrophenyl)benzothiazoles (Formula 5) (Hutchinson, I.; Chua, M. S.; Browne, H. L.; Trapani, V.; Bradshaw, T. D.; Westwell, A. D.; Stevens, M. F. G. *J. Med. Chem.* 2001, 44, 1446), followed by catalytic reduction of nitro group of Formula 5 with palladium on charcoal in methanol generated the target compounds 6 in excellent yields.

Chemical reagents were obtained without further purification. Solvents free distillated prior to use. Reactions were monitored by thin layer chromatography, using Merck plates 60 $F_{254}$. Flash chromatography was carried out on Merck Silica Gel 60 (40-63 lm) using the indicated solvents. Melting points were determined using Fargo MP-2D and are uncorrected. $^1$H NMR and $^{13}$C NMR spectra were recorded on Varian UNITY plus-400 at 400 and 100 MHz, respectively, using $CDCl_3$ as a solvent. 1H NMR chemical shifts are referenced to TMS or $CDCl_3$ (7.26 ppm). $^{13}$C NMR was referenced to $CDCl_3$ (77.0 ppm). Mass spectra were recorded with Bruker APEX II spectrometer. Elemental analyses were performed on Elementar vario EL III analyzer, and the results were found to be ±0.4% of the theoretical values. Purity of tested compounds was >95%.

General Procedure for the Syntheses of Benzamides (3a-3f) (Method a).

To a stirred solution of aniline (225 mmol, 1.2 equiv) in pyridine (450 mL) was added 4-nitrobenxzoyl chloride (186 mmol) under nitrogen at room temperature, then the mixture was refluxed for 4 h. After being cooled to room temperature, the solution was poured into ice/water. The resulting precipitate was filtered and recrystallized from methylene chloride to give the corresponding compounds 3.

4-Nitro-N-phenylbenzamide (3a). white solid; 91% yield; mp 214-216° C.; $^1$H NMR (CDCl$_3$, 400 MHz) δ9.42 (bs, NH), 8.38 (dt, J=2.4 and 3.6 Hz, 2H), 8.23 (dt, J=2.4 and 3.6 Hz, 2H), 7.85-7.82 (m, 2H), 7.40-7.35 (m, 2H), 7.17-7.13 (m, 1H); $^{13}$C NMR (CDCl$_3$, 100 MHz) δ165.3, 151.2, 142.6, 140.5, 130.5, 130.3, 125.8, 125.1, 121.8; HRMS (EI, m/z) for $C_{13}H_{10}N_2O_3$ calcd 242.0691, found 242.0692; Anal. calcd for $C_{13}H_{10}N_2O_3$: C, 64.46; H, 4.16; N, 11.56. Found, C, 64.72; H, 4.25; N, 11.54.

N-(4-Methylphenyl)-4-nitrobenzamide (3b). white solid; 93% yield; mp 201-203° C.; $^1$H NMR (CDCl$_3$, 400 MHz) δ9.37 (bs, NH), 8.26 (d, J=8.8 Hz, 2H), 8.11 (d, J=8.4 Hz, 2H), 7.58 (d, J=8.0 Hz, 2H), 7.16 (d, J=8.0 Hz, 2H), 2.34 (s, 3H); $^{13}$C NMR (CDCl$_3$, 100 MHz) δ163.8, 149.3, 140.7, 135.3, 134.4, 129.3, 128.7, 123.4, 120.8, 20.8; HRMS (ESI, m/z) for $C_{14}H_{12}N_2O_3Na$ calcd 279.0746, found 279.0744; Anal. calcd for $C_{14}H_{12}N_2O_3$: C, 65.62; H, 4.72; N, 10.93. Found C, 65.71; H, 5.00; N, 10.92.

N-(4-Ethylphenyl)-4-nitrobenzamide (3c). white solid; 96% yield; mp 186-188° C.; $^1$H NMR (CDCl$_3$, 400 MHz) δ8.32 (dd, J=5.2 and 1.6 Hz, 2H), 8.03 (d, J=8.4 Hz, 2H), 7.92 (bs, NH), 8.23 (d, J=8.0 Hz, 2H), 7.22 (d, J=8.4 Hz, 2H), 2.65 (q, J=7.6 Hz, 2H), 1.24 (t, J=7.2 Hz, 3H); $^{13}$C NMR (CDCl$_3$, 100 MHz) δ163.6, 149.6, 141.5, 140.6, 134.8, 128.6, 128.2, 124.0, 120.6, 28.4, 15.6; HRMS (ESI, m/z) for $C_{15}H_{15}N_2O_3$ calcd 271.1083, found 271.1084; Anal. calcd for $C_{15}H_{14}N_2O_3$: C, 66.66; H, 5.22; N, 10.36. Found C, 66.48; H, 5.41; N, 10.15.

N-(3-Methoxyphenyl)-4-nitrobenzamide (3d). yellow solid; 80% yield; mp 158-160° C.; $^1$H NMR (CDCl$_3$, 400 MHz) δ9.98 (bs, NH), 8.31~8.28 (m, 2H), 8.18 (d, J=8.8 Hz, 2H), 7.94 (s, 1H), 7.32~7.23 (m, 2H), 6.72~6.69 (m, 1H), 3.82 (s, 3H); $^{13}$C NMR (CDCl$_3$, 100 MHz) δ163.8, 159.5, 149.0, 140.5, 139.2, 129.1, 128.7, 123.0, 112.8, 109.9, 106.3, 54.9; HRMS (ESI, m/z) for $C_{14}H_{12}N_2O_4Na$ calcd 295.0695, found 295.0694; Anal. Calcd for $C_{14}H_{12}N_2O_4$: C, 61.76; H, 4.44; N, 10.29. Found C, 61.49; H, 4.59; N, 10.33.

N-(4-Methoxyphenyl)-4-nitrobenzamide (3e). yellow solid; 80% yield; mp 196-197° C.; $^1$H NMR (CDCl$_3$, 400 MHz) δ9.35 (bs, NH), 8.22 (d, J=8.0 Hz, 2H), 8.07 (d, J=8.0 Hz, 2H), 7.68 (d, J=8.4 Hz, 1H), 6.95 (d, J=8.4 Hz, 2H), 3.75 (s, 3H); $^{13}$C NMR (CDCl$_3$, 100 MHz) δ163.7, 156.6, 149.2, 140.7, 130.9, 128.6, 123.3, 122.5, 113.9, 55.3; HRMS (ESI, m/z) for $C_{14}H_{13}N_2O_4$ calcl 273.0875, found 273.0873; Anal. Calcd for $C_{14}H_{12}N_2O_4$: C, 61.76; H, 4.44; N, 10.29. Found C, 61.88; H, 4.65; N, 10.14.

N-(4-Trifluoromethylphenyl)-4-nitrobenzamide (3f). white solid; 95% yield; mp 194-196° C.; $^1$H NMR (DMSO, 400 MHz) δ10.87 (bs, NH), 8.37 (d, J=8.4 Hz, 2H), 8.14 (d, J=8.4 Hz, 2H), 7.97 (d, J=8.0 Hz, 2H), 7.70 (d, J=8.4 Hz, 2H); $^{13}$C NMR (DMSO, 100 MHz) δ164.9, 149.6, 142.5, 140.3, 129.6, 126.3, 124.5 (q, J=140 Hz, 1C), 123.9, 120.7, 114.1; HRMS (EI, m/z) for $C_{14}H_9F_3N_2O_3$ calcd 310.0560, found 310.0563; Anal. calcd for $C_{14}H_9F_3N_2O_3$: C, 54.20; H, 2.92; N, 9.03. Found C, 54.50; H, 2.84; N, 9.25.

General Procedure for the Syntheses of Benzamides (3g-3j) (Method b)

To a stirred solution of 4-nitrobenzoic acid (82 mmol) in benzene (165 ml) was treated with thionyl chloride (58 mL, 820 mmol, 10 equiv) under nitrogen at room temperature then the mixture was reflux for 4 h. After removal of solvent, the benxzoyl chloride intermediate was added slowly to a solution of the appropriately substituted aniline (123 mmol, 1.5 equiv) in pyridine (165 ml). The mixture was refluxed under nitrogen at room temperature for 4 h. After being cooled room temperature, the solution was poured into ice/water. The resulting precipitate was filtered and recrystallized from methylene chloride to give the corresponding compounds 3.

N-(Phenyl)-3-methyl-4-nitrobenzamide (3g). white solid; 82% yield; mp 149-151° C.; $^1$H NMR (CDCl$_3$, 400 MHz) δ8.01 (d, J=8.4 Hz, 1H), 7.98 (bs, NH), 7.84 (s, 1H), 7.78 (d, J=8.4 Hz, 2H), 7.63 (d, J=7.6 Hz, 2H), 7.40-7.36 (m, 2H), 7.21-7.17 (m, 1H), 2.64 (s, 3H); $^{13}$C NMR (CDCl$_3$, 100 MHz) δ163.9, 150.9, 138.8, 137.27, 134.2, 131.8, 139.2, 125.4, 125.3, 125.0, 120.4, 20.3; HRMS (ESI, m/z) for $C_{14}H_{13}N_2O_3$ calcd 257.0926, found 257.0925; Anal. calcd for $C_{14}H_{12}N_2O_3$: C, 65.62; H, 4.72; N, 10.93. Found C, 65.53; H, 4.60; N, 11.00.

N-(4-Ethylphenyl)-3-methyl-4-nitrobenzamide (3h). white solid; 80% yield; mp 137-139° C.; $^1$H NMR (CDCl$_3$, 400 MHz) δ8.03 (bs, NH), 7.97 (d, J=8.4 Hz, 1H), 7.82 (s, 1H), 7.75 (d, J=8.4 Hz, 1H), 7.52 (d, J=8.4 Hz, 2H), 7.29 (d, J=8.0 Hz, 2H), 2.67-2.61 (m, 5H), 1.24 (t, J=8.4 Hz, 3H); $^{13}$C NMR (CDCl$_3$, 100 MHz) δ163.8, 150.8, 141.4, 138.9, 134.9, 134.1, 131.8, 128.5, 125.4, 125.0, 120.6, 28.3, 20.3, 15.6;

HRMS (ESI, m/s) for $C_{16}H_{17}N_2O_3$ calcd 285.1239, found 285.1241; Anal. calcd for $C_{16}H_{16}N_2O_3$: C, 67.59; H, 5.67; N, 9.85. Found C, 67.50; H, 5.45; N, 9.85.

N-(4-Methoxyphenyl)-3-methyl-4-nitrobenzamide (3i). white solid; 71% yield; mp 152-154° C.; $^1$H NMR (CDCl$_3$, 400 MHz) δ7.98 (d, J=8.4 Hz, 1H), 7.94 (bs, NH), 7.81 (s, 1H), 7.75 (d. J=8.0 Hz, 1H), 7.52 (d, J=8.8 Hz, 2H), 6.89 (d, J=9.2 Hz, 2H), 3.81 (s, 3H), 2.62 (s, 3H); $^{13}$C NMR (CDCl$_3$, 100 MHz) δ163.7, 157.0, 150.8, 138.8, 134.1, 131.7, 130.2, 125.3, 124.9, 122.3, 114.3, 114.2, 55.4, 20.2; HRMS (ESI, m/z) for $C_{15}H_{15}N_2O_4$ calcd 287.1032, found 287.1033; Anal. calcd for $C_{15}H_{14}N_2O_4$: C, 62.93; H, 4.93; N, 9.79. Found C, 62.77; H, 5.17; N, 9.82.

3-Methyl-4-nitro-N-(4-trifluoromethyl-phenyl)benzamide (3j). white solid; 75% yield; mp 154-156° C.; $^1$H NMR (CDCl$_3$, 400 MHz) δ9.38 (bs, NH), 8.01 (d, J=8.8 Hz, 1H), 7.92 (s, 1H), 7.87-7.83 (m, 2H), 7.61 (d, J=8.4 Hz, 2H), 2.64 (s, 3H); $^{13}$C NMR (CDCl$_3$, 100 MHz) δ164.8, 150.8, 141.0, 138.4, 133.8, 132.1, 126.1 (q, J=38 Hz, CF3-C), 125.8, 124.7, 123.2 (q, J=140 Hz, CF3), 120.3, 120.2 20.0; HRMS (EI, m/z) for $C_{15}H_{11}N_2O_2F_3$ calcd 324.0722, found 324.0725; Anal. calcd for $C_{15}H_{11}F_3N_2O_3$: C, 55.56; H, 3.42; N, 8.64. Found, C, 55.50; H, 3.48; N, 8.64.

General Procedure for the Syntheses of Thiobenzamide (4a-4-j).

A mixture of the substituted 4-nitro-N-phenylbenzamide (41 mmol) and Lawesson's reagent (8.52 g, 21 mmol, 0.51 equiv) in chlorobenzene (30 ml) was heated at reflux for 4-6 h, after which it was concentrated, purified by column chromatography (CH$_2$Cl$_2$/hexane=2:3) to give the corresponding compounds 4.

4-Nitro-N-phenylthiobenzamide (4a). yellow solid; 60% yield; mp 154-156° C.; $^1$H NMR (CDCl$_3$, 400 MHz) δ9.08 (bs, NH), 8.26 (d, J=8.4 Hz, 2H), 7.95 (d, J=8.4 Hz, 2H), 7.77 (d, J=7.6 Hz, 2H), 7.47 (t, J=8.0 Hz, 2H), 7.34 (t, J=8.0 Hz, 1H); $^{13}$C NMR (CDCl$_3$, 100 MHz) δ195.5, 148.9, 148.2, 138.5, 129.2, 127.7, 127.5, 123.9, 123.5; HRMS (EI, m/z) for $C_{13}H_{10}N_2O_2S$ calcd 258.0463, found 258.0463; Anal. calcd for $C_{13}H_{10}N_2O_2S$, C, 60.45; H, 3.90; N, 10.85. Found C, 60.44; H, 4.06; N, 10.75.

N-(4-Methylphenyl)-4-nitrothiobenzamide (4b). yellow solid; 60% yield; mp 195-196° C.; $^1$H NMR (CDCl$_3$, 400 MHz) δ9.15 (bs, NH), 8.21 (d, J=8.4 Hz, 2H), 7.91 (d, J=8.8 Hz, 2H), 7.60 (d, J=8.4 Hz, 2H), 7.26-7.23 (m, 2H), 2.38 (s, 3H); $^{13}$C NMR (CDCl$_3$, 100 MHz) δ195.27, 148.8, 148.0, 137.6, 135.9, 129.7, 127.7, 123.8, 123.6, 21.2; HRMS (ESI, m/z) for $C_{14}H_{12}N_2O_2SNa$ calcd 295.0517, found 295.0516; Anal. calcd for $C_{14}H_{12}N_2O_2S$: C, 61.75; H, 4.44; N, 10.29. Found C, 61.81; H, 4.55; N, 10.29.

N-(4-Ethylphenyl)-4-nitrothiobenzamide (4c). yellow solid; 65% yield; mp 142-144° C.; $^1$H NMR (CDCl$_3$, 400 MHz) δ9.07 (bs, NH), 8.25 (d, J=8.4 Hz, 2H), 7.94 (d, J=8.8 Hz, 2H), 7.66 (d, J=8.4 Hz, 2H), 7.28 (d, J=8.0 Hz, 2H), 2.69 (q, J=8.0 Hz 2H), 1.27 (t, J=7.6 Hz, 3H); $^{13}$C NMR (CDCl$_3$, 100 MHz) δ195.2, 148.9, 148.2, 143.9, 136.1, 128.9, 128.6, 127.7, 123.9, 123.5, 28.5, 15.3; HRMS (ESI, m/z) for $C_{15}H_{15}N_2O_2S$ calcd 287.0854, found 287.0856; Anal. calcd for $C_{15}H_{14}N_2O_2S$: C, 62.92; H, 4.93; N, 9.78. Found C, 62.91; H, 4.95; N, 9.60.

N-(3-Methoxyphenyl)-4-nitrothiobenzamide (4d). yellow solid; 64% yield; mp 138-140° C.; $^1$H NMR (CDCl$_3$, 400 MHz) δ10.61 (bs, NH), 8.23 (d, J=8.8 Hz, 2H), 7.96 (d, J=8.8 Hz, 2H), 7.60 (s, 1H), 7.36-7.30 (m, 2H), 6.86-6.83 (m, 1H), 3.83 (s, 3H); $^{13}$C NMR (CDCl$_3$, 100 MHz) δ195.3, 159.8, 148.8, 148.2, 146.2, 129.6, 128.2, 123.3, 115.8, 112.7, 109.2, 55.4; HRMS (ESI, m/z) for $C_{14}H_{12}N_2O_3SNa$ calcd 311.0466, found 311.0464; Anal. calcd for $C_{14}H_{12}N_2O_3S$: C, 58.32; H, 4.20; N, 9.72. Found, C, 58.25; H, 4.36; N, 9.61.

N-(4-Methoxyphenyl)-4-nitrothiobenzamide (4e). yellow solid; 62% yield; mp 174-175° C.; $^1$H NMR (CDCl$_3$, 400 MHz) δ9.98 (bs, NH), 8.31-8.28 (m, 2H), 8.18 (d, J=8.8 Hz, 2H), 7.94 (s, 1H), 7.32-7.23 (m, 2H), 6.72~6.69 (m, 1H), 3.82 (s, 3H); $^{13}$C NMR (CDCl$_3$, 100 MHz) δ163.8, 159.5, 149.0, 140.5, 139.2, 129.1, 128.7, 123.0, 112.8, 109.9, 106.3, 54.85; HRMS (EI, m/z) for $C_{14}H_{12}N_2O_3S$ calcd 288.0569, found 288.0571; Anal. calcd for $C_{14}H_{12}N_2O_3S$: C, 58.32; H, 4.20; N, 9.72. Found C, 58.29; H, 4.42; N, 9.47.

N-(4-Trifluoromethylphenyl)-4-nitrothiobenzamide (4f). yellow solid; 71% yield; mp 174-175° C.; $^1$H NMR (CDCl$_3$, 400 MHz) δ11.49 (bs, NH), 8.25 (d, J=8.4 Hz, 2H), 8.07 (d, J=8.8 Hz, 2H), 7.99 (d, J=8.4 Hz, 2H), 7.68 (d, J=8.0 Hz, 2H); $^{13}$C NMR (CDCl$_3$, 100 MHz) δ196.1, 148.5, 148.0, 142.4, 128.4, 125.8, 125.8, 123.5, 123.1, 122.3 (q, J=140 Hz, CF$_3$); HRMS (ESI, m/z) for $C_{14}H_{10}N_2O_2F_3S$ calcd 326.0337, found 326.0335. Anal. calcd for $C_{14}H_{10}N_2O_2F_3S$: C, 51.53; H, 2.78; N, 8.59. Found C, 51.90; H, 2.86; N, 8.63.

N-(Phenyl)-3-methyl-4-nitrothiobenzamide (4g). yellow solid; 72% yield; mp 118-120° C.; $^1$H NMR (CDCl$_3$, 400 MHz) δ9.09 (bs, NH), 7.99 (d, J=8.4 Hz, 1H), 7.78-7.71 (m, 4H), 7.46 (t, J=8.0 Hz, 2H), 7.33 (t, J=7.6 Hz, 1H), 2.64 (s, 3H); $^{13}$C NMR (CDCl$_3$, 100 MHz) δ195.7, 146.6, 138.5, 134.2, 131.2, 129.2, 127.4, 125.1, 124.8, 123.5, 20.5; HRMS (ESI, m/z) for $C_{14}H_{13}N_2O_2S$ calcd 273.0698, found 273.0700; Anal. calcd for $C_{14}H_{13}N_2O_2S$: C, 61.75; H, 4.44; N, 10.29. Found C, 62.01; H, 4.39; N, 10.26.

N-(4-Ethylphenyl)-3-methyl-4-nitrothiobenzamide (4h). yellow solid; 70% yield; mp 160-162° C.; $^1$H NMR (CDCl$_3$, 400 MHz) δ9.03 (bs, NH), 7.99 (d, J=8.4 Hz, 1H), 7.78-7.65 (m, 3H), 7.28 (d, J=8.4 Hz, 2H), 2.72-2.64 (m, 5H), 1.26 (t, J=7.6 Hz, 3H); $^{13}$C NMR (CDCl$_3$, 100 MHz) δ195.4, 150.1, 146.6, 143.8, 136.1, 134.2, 131.3, 128.5, 125.0, 124.81 123.5, 28.5, 20.5, 15.4; HRMS (ESI, m/z) for $C_{16}H_{17}N_2O_2S$ calcd 301.1011, found 301.1012; Anal. calcd for $C_{16}H_{17}N_2O_2S$: C, 63.98; H, 5.37; N, 9.33. Found C, 63.99; H, 5.39; N, 9.30.

N-(4-Methoxyphenyl)-3-methyl-4-nitrothiobenzamide (4i). yellow solid; 61% yield; mp 160-162° C.; $^1$H NMR (CDCl$_3$, 400 MHz) δ10.81 (bs, NH), 7.96 (d, J=8.1 Hz, 1H), 7.83 (dd, J=1.6 and 0.8 Hz, 1H), 7.77 (dd, J=8.4 and 2.0 Hz, 1H), 7.69 (dt, J=8.8 and 3.2 Hz, 1H), 6.94 (dt, J=8.8 and 3.2 Hz, 2H), 3.83 (s, 3H), 2.63 (s, 3H); $^{13}$C NMR (CDCl$_3$, 100 MHz) δ195.0, 157.9, 149.5, 146.2, 133.3, 132.2, 131.7, 125.4, 124.3, 113.7, 55.2, 20.2; HRMS (ESI, m/z) for $C_{15}H_{15}N_2O_3S$ calcd 303.0803, found 303.0804; Anal. calcd for $C_{15}H_{15}N_2O_3S$: C, 59.59; H, 4.67; N, 9.27. Found C, 59.95; H, 4.90; N, 9.07.

3-Methyl-4-nitro-N-(4-trifluoromethylphenyl)thiobenzamide (4j). yellow solid; 74% yield; mp 170-172° C.; 1H NMR (CDCl3, 400 MHz) δ8.04-7.98 (m, 3H), 7.81-7.68 (m, 4H), 2.65 (s, 3H); 13C NMR (CDCl3, 100 MHz) δ208.5, 196.6, 149.8, 146.4, 142.2, 133.5, 131.5, 125.8, 125.3, 124.4, 123.5, 122.3 (q, J=140 Hz, CF3), 29.7, 20.0; HRMS (ESI, m/z) for C15H11N2O2SF3 calcd 340.0493, found 340.0494; Anal. calcd for C15H11N2O2SF3: C, 52.94; H, 3.26; N, 8.23. Found C, 52.68; H, 3.47; N, 8.27.

General Procedure for the Syntheses of 2-(4-Nitrophenyl) Benzothiazole (5a-5j).

A solution of substituted 4-nitrothiobenzamides (50 mmol) in 3 drops of 95% EtOH and 30% aqueous sodium hydroxide solution (10.6 mL, 8 equiv) was added dropwise to a solution of potassium ferricyanide (13.16 g, 4 equiv) in water (50 mL) at 90° C. The reaction mixture was heated for a further 1 h and then cooled in ice. The resulting precipitate was filtered and washed with water, then subjected to flash chromatography (CH$_2$Cl$_2$/hexane=1:4) to give the corresponding compounds 5.

2-(4-Nitrophenyl)benzothiazole (5a). white solid; 68% yield; mp 228-230° C.; $^1$H NMR (CDCl$_3$, 400 MHz) δ8.35 (dt, J=9.2 and 2.0 Hz, 2H), 8.27 (dt, J=9.2 and 2.0 Hz, 2H), 8.13 (d, J=8.0 Hz, 1H), 7.96 (d, J=8.0 Hz, 1H), 7.56 (dt, J=8.0 and 1.2 Hz, 1H), 7.47 (dt, J=8.0 and 1.2 Hz, 1H); $^{13}$C NMR (CDCl$_3$, 100 MHz) δ164.8, 154.1, 149.0, 139.1, 135.4, 128.2, 126.9, 126.2, 124.3, 123.9, 121.8; HRMS (EI, m/z) for C$_{13}$H$_8$N$_2$O$_2$S calcd 256.0306, found 256.0308; Anal. calcd for C$_{13}$H$_8$N$_2$O$_2$S: C, 60.93; H, 3.15; N, 10.93. Found C, 60.89; H, 3.34; N, 10.75.

6-Methyl-2-(4-nitrophenyl)benzothiazole (5b). white solid; 65% yield; mp 148-150; $^1$H NMR (CDCl$_3$, 400 MHz) δ8.31 (s, 1H), 8.23 (s, 2H), 7.99 (d, J=6.4 Hz, 1H), 7.72 (s, 1H), 7.36 (s, 1H), 2.52 (s, 3H); $^{13}$C NMR (CDCl$_3$, 100 MHz) δ163.7, 152.2, 148.8, 139.3, 136.6, 135.6, 128.5, 128.0, 124.2, 123.3, 121.4, 21.6; HRMS (EI, m/z) for C$_{14}$H$_{12}$N$_2$O$_2$S calcd 295.0517, found 295.0516; Anal. calcd for C$_{14}$H$_{10}$N$_2$O$_2$S: C, 62.21; H, 3.73; N, 10.36. Found, C, 62.37; H, 3.91; N, 10.31.

6-Ethyl-2-(4-nitrophenyl)benzothiazole (5c). white solid; 72% yield; mp 151-152; $^1$H NMR (CDCl$_3$, 400 MHz) δ8.34 (dd, J=0.8 and 2.0 Hz, 2H), 8.25 (dd, J=4.8 and 2.0 Hz, 2H), 8.02 (d, J=8.4 Hz, 1H), 7.76 (d, J=0.8 Hz, 1H), 7.40 (dd, J=8.4 and 1.6 Hz, 1H), 2.28 (q, J=7.6 Hz, 2H), 1.33 (t, J=7.6 Hz, 3H); $^{13}$C NMR (CDCl$_3$, 100 MHz) δ163.8, 152.4, 148.8, 143.0, 139.3, 135.7, 128.0, 127.6, 124.3, 123.5, 120.3, 29.0, 15.7; HRMS (ESI, m/z) for C$_{15}$H$_{12}$N$_2$O$_2$S calcd 285.0698, found 285.0695; Anal. calcd for C$_{15}$H$_{12}$N$_2$O$_2$S: C, 63.36; H, 4.25; N, 9.85. Found C, 63.40; H, 4.55; N, 9.53.

7-Methoxy-2-(4-nitrophenyl)benzothiazole (5d). white solid; 25% yield; mp 228-230; $^1$H NMR (CDCl$_3$, 400 MHz), δ8.33 (d, J=8.8 Hz, 2H), 8.25 (d, J=8.8 Hz, 2H), 7.75-7.73 (m, 1H), 7.49 (t, J=8.4 Hz, 1H), 6.89 (d, J=8.4 Hz, 1H), 4.03 (s, 3H); $^{13}$C NMR (CDCl$_3$, 100 MHz) δ165.4, 155.6, 154.3, 148.9, 139.2, 128.2, 127.8, 124.3, 116.4, 105.9, 56.0; HRMS (ESI, m/z) for C$_{14}$H$_{10}$N$_2$O$_3$SNa calcd 309.0310, found 309.0308; Anal. calcd for C$_{14}$H$_{10}$N$_2$O$_3$S: C, 58.73; H, 3.52; N, 9.78. Found C, 58.94; H, 3.70; N, 9.65.

6-Methoxy-2-(4-nitrophenyl)benzothiazole (5e). yellow solid; 63% yield; mp 214-216; $^1$H NMR (CDCl$_3$, 400 MHz) δ8.33 (dt, J=9.2 and 2.0 Hz, 2H), 8.20 (dt, J=9.2 and 2.0 Hz, 2H), 8.00 (d, J=9.2 Hz, 1H), 7.38 (d, J=2.4 Hz, 1H), 7.15 (dd, J=9.2 and 2.4 Hz, 1H), 3.92 (s, 3H); $^{13}$C NMR (CDCl$_3$, 100 MHz) δ162.2, 158.5, 148.7, 148.6, 139.3, 137.0, 127.8, 124.5, 124.2, 116.6, 104.0, 55.8; HRMS (ESI, m/z) for C$_{14}$H$_{11}$N$_2$O$_3$S calcd 287.0490, found 287.0492. Anal. calcd for C$_{14}$H$_{10}$N$_2$O$_3$S: C, 58.73; H, 3.52; N, 9.78. Found C, 58.68; H, 3.47; N, 9.75.

2-(4-Nitrophenyl)-6-trifluoromethyl-benzothiazole (5f). yellow solid; 61% yield; mp 149-151; $^1$H NMR (CDCl$_3$, 400 MHz) δ8.35 (dt, J=9.2 and 2.0 Hz, 2H), 8.27-8.23 (m, 3H), 8.19 (d, J=8.4 Hz, 1H), 7.77 (dd, J=8.4 and 2.0 Hz, 1H); $^{13}$C NMR (CDCl$_3$, 100 MHz) δ167.8, 155.8, 149.4, 138.3, 135.4, 128.4, 128.2, 124.3, 124.2, 123.9, 123.8, 119.5; HRMS (ESI, m/z) for C$_{14}$H$_7$N$_2$O$_2$SF$_3$ calcd 324.0175, found 324.0178; Anal. calcd for C$_{14}$H$_7$N$_2$O$_2$SF$_3$: C, 51.85; H, 2.18; N, 8.64. Found C, 51.86; H, 2.22; N, 8.69.

2-(3-Methyl-4-nitrophenyl)benzothiazole (5g). white solid; 71% yield; mp 163-165; $^1$H NMR (CDCl$_3$, 400 MHz) δ8.13-8.08 (m, 3H), 8.02 (dd, J=8.0 and 2.0 Hz, 1H), 7.95 (dd, J=8.0 and 1.2 Hz, 1H), 7.55 (dt, J=8.0 and 1.2 Hz, 1H), 7.45 (dt, J=8.0 and 1.2 Hz, 1H), 2.71 (s, 3H); $^{13}$C NMR (CDCl$_3$, 100 MHz) δ165.1, 153.9, 150.1, 137.4, 135.4, 134.7, 131.4, 126.8, 126.0, 125.8, 125.5, 123.7, 121.8, 20.6; HRMS (ESI, m/z) for C$_{14}$H$_{11}$N$_2$O$_2$S calcd 271.0541, found 271.0541. Anal. calcd for C$_{14}$H$_{11}$N$_2$O$_2$S: C, 62.21; H, 3.73; N, 10.36. Found C, 62.07; H, 3.88; N, 10.26.

6-Ethyl-2-(3-methyl-4-nitrophenyl)benzothiazole (5h). yellow solid; 75% yield; mp 118-120; $^1$H NMR (CDCl$_3$, 400 MHz) δ8.10 (d, J=8.8 Hz, 1H), 8.08 (s, 1H), 8.02 (d, J=8.4 Hz, 1H), 8.01 (dd, J=8.4 and 2.0 Hz, 1H), 7.75 (d, J=2.0 Hz, 1H), 7.38 (dd, J=8.4 and 2.0 Hz, 1H), 2.83 (q, J=7.6 Hz, 2H), 2.71 (s, 3H), 1.33 (t, J=7.6 Hz, 3H); $^{13}$C NMR (CDCl$_3$, 100 MHz) δ164.1, 152.4, 149.9, 142.8, 137.7, 135.6, 134.6, 131.3, 127.4, 125.6, 125.5, 123.3, 120.3, 29.0, 20.6, 15.7; HRMS (ESI, m/z) for C$_{16}$H$_{15}$N$_2$O$_2$S calcd 299.0854, found 299.0856; Anal. calcd for C$_{16}$H$_{15}$N$_2$O$_2$S: C, 64.41; H, 4.73; N, 9.39. Found C, 64.20; H, 4.80; N, 9.14.

6-Methoxy-2-(3-methyl-4-nitrophenyl)benzothiazole (5i). yellow solid; 64% yield; mp 195-197; $^1$H NMR (CDCl$_3$, 400 MHz) δ8.07 (d, J=8.8 Hz, 1H), 8.02 (d, J=0.8 Hz, 1H), 7.98 (d, J=9.2 Hz, 1H), 7.95 (dd, J=8.4 and 2.0 Hz, 1H), 7.36 (d, J=2.4 Hz, 1H), 7.14 (dd, J=9.2 and 2.4 Hz, 1H), 3.90 (s, 3H), 2.71 (s, 3H); $^{13}$C NMR (CDCl$_3$, 100 MHz) δ162.3, 158.4, 149.6, 148.6, 137.6, 136.8, 134.6, 130.9, 125.5, 125.3, 124.3, 116.4, 103.9, 55.8, 20.6; HRMS (ESI, m/z) for C$_{15}$H$_{14}$N$_2$O$_3$S calcd 301.0647, found 301.0648. Anal. calcd for C$_{15}$H$_{14}$N$_2$O$_3$S: C, 59.93; H, 4.03; N, 9.33. Found C, 60.37 H, 4.13; N, 9.36.

2-(3-Methyl-4-nitrophenyl)-6-trifluoromethylbenzothiazole (5j). yellow solid; 30% yield; mp 99-101; $^1$H NMR (CDCl$_3$, 400 MHz) δ8.21-8.15 (m, 2H), 8.08-8.06 (m, 2H), 8.00 (dd, J=8.8 and 1.6 Hz, 1H), 7.76 (dd, J=8.8 and 1.6 Hz, 1H), 2.69 (s, 3H); $^{13}$C NMR (CDCl$_3$, 100 MHz) δ168.0, 155.7, 150.4, 136.6, 135.2134.6, 131.60, 127.9 (q, J=32.6 Hz, 1C), 125.9 (d, J=43.2 Hz, 1C), 125.49, 124.08, 123.8, 122.2, 119.4 (q, J=4.5 Hz, 1C), 20.4; HRMS (ESI, m/z) for C$_{15}$H$_{10}$N$_2$O$_2$F$_3$S calcd 339.0415, found 339.0414; Anal. calcd for C$_{15}$H$_9$N$_2$O$_2$F$_3$S: C, 53.25; H, 2.68; N, 8.28. Found C, 53.21; H, 2.73; N, 8.14.

General Procedure for the Syntheses of 2-(4-Aminophenyl)Benzothiazole (6a-6j).

To a solution of 2-(4-nitrophenyl)benzothiazole (1 g, 3.9 mmol) in CH$_2$Cl$_2$ (30 ml) was added 10% Pd/C (0.1 g) under hydrogen at room temperature for 4 h. The resulting solution was concentrated and subjected to flash chromatography (CH$_2$Cl$_2$) to give the corresponding compounds 6.

2-(4-Aminophenyl)benzothiazole (6a). yellow solid; 94% yield; mp 130-132; $^1$H NMR (CDCl$_3$, 400 MHz) δ7.99 (m, 1H), 7.89 (m, 2H), 7.84 (m, 1H), 7.44 (m, 1H), 7.32 (m, 1H), 6.72 (dt, J=4.2 and 2.0 Hz, 2H), 4.00 (bs, NH$_2$); $^{13}$C NMR (CDCl$_3$, 100 MHz) δ168.5, 154.2, 149.2, 134.6, 129.1, 126.0, 124.4, 123.9, 122.5, 121.4, 114.8; HRMS (ESI, m/z) for C$_{13}$H$_{10}$N$_2$S calcd 226.0565, found 226.0567; Anal. calcd for C$_{13}$H$_{10}$N$_2$S: C, 69.00; H, 4.45; N, 12.38. Found C, 69.01; H, 4.69; N, 12.29.

2-(4-Aminophenyl)-6-methylbenzothiazole (6b). yellow solid; 95% yield; mp 181-183; $^1$H NMR (CDCl$_3$, 400 MHz) δ7.88-7.85 (m, 3H), 7.63 (s, 1H), 7.25 (dd, J=6.8 and 1.6 Hz, 1H), 6.71 (dd, J=4.4 and 2.4 Hz, 1H), 7.32 (m, 1H), 6.72 (dt, J=4.2 and 2.0 Hz, 2H), 4.00 (bs, NH$_2$), 2.46 (s, 3H); $^{13}$C NMR (CDCl$_3$, 100 MHz) δ167.5, 152.3, 149.0, 134.7, 134.5, 129.5, 129.0, 127.6, 126.3, 124.1, 122.0, 121.2, 114.8, 21.5; HRMS (ESI, m/z) for C$_{14}$H$_{13}$N$_2$S calcd 241.0799, found 241.0798; Anal. calcd for C$_{14}$H$_{12}$N$_2$S: C, 69.97; H, 5.03; N, 11.66. Found C, 69.84; H, 5.01; N, 11.70.

2-(4-Aminophenyl)-6-ethylbenzothiazole (6c). yellow solid; 92% yield; mp 154-156; $^1$H NMR (CDCl$_3$, 400 MHz) δ7.90-7.86 (m, 3H), 7.65 (t, J=0.4 Hz, 1H), 7.27 (dd, J=7.6 and 2.0 Hz, 1H), 6.81 (dt, J=4.8 and 2.0 Hz, 2H), 3.98 (bs, NH$_2$), 2.76 (q, J=7.6 Hz, 2H), 1.29 (t, J=7.6 Hz, 3H); $^{13}$C NMR (CDCl$_3$, 100 MHz) δ167.6, 152.5, 149.0, 141.0, 134.7, 129.0, 126.5, 124.1, 122.1, 114.7, 28.87, 15.8; HRMS (ESI, m/z) for C$_{15}$H$_{14}$N$_2$OSNa calcd 277.0775, found 277.0776. Anal. calcd for C$_{15}$H$_{14}$N$_2$S: C, 70.83; H, 5.55; N, 11.01. Found C, 70.62; H, 5.29; N, 10.90.

2-(4-Aminophenyl)-7-methoxybenzothiazole (6d). yellow solid; 95% yield; mp 142-144; $^1$H NMR (CDCl$_3$, 400 MHz) δ7.90 (d, J=8.4 Hz, 2H), 7.62 (d, J=8.0 Hz, 1H), 7.39 (t, J=8.0 Hz, 1H), 6.78 (d, J=8.0 Hz, 1H), 6.73 (d, J=8.4 Hz, 2H), 3.99 (s, 5H); $^{13}$C NMR (CDCl$_3$, 100 MHz) δ169.1, 15.9, 154.2, 149.2, 129.1, 126.9, 124.0, 123.0, 115.3, 114.8, 104.7, 55.9; HRMS (ESI, m/z) for C$_{14}$H$_{13}$N$_2$OS calcd 257.0749, found 257.0748; Anal. calcd for C$_{14}$H$_{12}$N$_2$OS: C, 65.60; H, 4.72; N, 10.93. Found C, 65.66; H, 4.86; N, 10.92.

2-(4-Aminophenyl)-6-methoxybenzothiazole (6e). yellow solid; 96% yield; mp 174-176; $^1$H NMR (CDCl$_3$, 400 MHz) δ7.88 (s, 1H), 7.84 (dt, J=4.8 and 2.8 Hz, 2H), 7.32 (d, J=2.4 Hz, 1H), 7.04 (dd, J=4.8 and 2.4 Hz, 1H), 7.73 (dt, J=4.8 and 2.8 Hz, 2H), 3.98 (bs, NH$_2$), 3.87 (s, 3H); $^{13}$C NMR (CDCl$_3$, 100 MHz) δ166.1, 157.3, 148.8, 148.8, 135.9, 135.9, 128.8, 124.2, 123.0, 115.1, 114.8, 104.3, 55.8; HRMS (ESI, m/z) for C$_{14}$H$_{13}$N$_2$OS calcd 257.0749, found 257.0748; Anal. calcd for C$_{14}$H$_{12}$N$_2$OS: C, 65.60; H, 4.72; N, 10.93. Found C, 65.35; H, 4.90; N, 10.67.

2-(4-Aminophenyl)-6-trifluoromethylbenzothiazole (6f). yellow solid; 91% yield; mp 181-183; $^1$H NMR (CDCl$_3$, 400 MHz) δ8.11 (s, 1H), 8.03 (d, J=8.4 Hz, 1H), 7.90 (dt, J=4.8 and 2.4 Hz, 2H), 7.67 (dd, J=6.8 and 1.6 Hz, 1H), 6.73 (dt, J=4.8 and 2.4 Hz, 2H), 4.08 (bs, NH$_2$); $^{13}$C NMR (CDCl$_3$, 100 MHz) δ169.9, 158.1, 149.9, 132.3, 129.4, 123.1, 123.0, 122.5, 119.0, 119.0, 114.7; HRMS (ESI, m/z) for C$_{14}$H$_9$F$_3$N$_2$S calcd 294.0439, found 294.0438; Anal. calcd for C$_{14}$H$_9$F$_3$N$_2$S: C, 57.14; H, 3.08; N, 9.52. Found C, 57.20; H, 3.18; N, 9.49.

2-(4-Amino-3-methylphenyl)benzothiazole (6g). yellow solid; 94% yield; mp 147-149; $^1$H NMR (CDCl$_3$, 400 MHz) δ7.99 (d, J=8.0 Hz, 1H), 7.85-7.83 (m, 2H), 7.75 (dd, J=8.0 and 2.0 Hz, 1H), 7.44 (td, J=8.0 and 1.2 Hz, 1H), 7.31 (td, J=8.0 and 1.2 Hz, 1H), 6.71 (d, J=8.0 Hz, 1H), 3.94 (bs, NH$_2$), 2.23 (s, 3H); $^{13}$C NMR (CDCl$_3$, 100 MHz) δ168.7, 154.2, 147.5, 134.5, 129.7, 126.9, 126.0, 124.3, 123.8, 122.4, 122.1, 121.3, 114.5, 17.1; HRMS (ESI, m/z) for C$_{14}$H$_{12}$N$_2$OSNa calcd 263.0619, found 263.0618. Anal. calcd for C$_{14}$H$_{12}$N$_2$OS: C, 69.97; H, 5.03; N, 11.66. Found C, 69.84; H, 5.01; N, 11.70.

2-(4-Amino-3-methylphenyl)-6-ethylbenzothiazole (6h). yellow solid; 93% yield; mp 171-173; $^1$H NMR (CDCl$_3$, 400 MHz) δ7.90 (d, J=8.4 Hz, 1H), 7.80 (d, J=1.6 Hz, 1H), 7.32 (dd, J=6.0 and 2.4 Hz, 1H), 7.65 (d, J=0.8 Hz, 1H), 7.27 (dd, J=6.8 and 1.6 Hz, 1H), 6.70 (d, J=8.4 Hz, 1H), 3.92 (bs, NH$_2$), 2.76 (q, J=8.0 Hz, 2H), 2.22 (s, 3H), 1.29 (t, J=7.6 Hz, 3H); $^{13}$C NMR (CDCl$_3$, 100 MHz) δ167.8, 152.5, 147.4, 140.9, 140.9, 134.7, 129.6, 126.8, 126.5, 124.1, 122.1, 122.0, 120.0, 114.6, 28.9, 17.2, 15.8; HRMS (ESI, m/z) for C$_{16}$H$_{17}$N$_2$OS calcd 269.1112, found 269.1110; Anal. calcd for C$_{16}$H$_{16}$N$_2$S: C, 71.61; H, 6.01; N, 10.44. Found C, 72.01; H, 6.36; N, 10.52.

2-(4-Amino-3-methylphenyl)-6-methoxybenzothiazole (6i). yellow solid; 95% yield; mp 151-153; $^1$H NMR (CDCl$_3$, 400 MHz) δ7.87 (d, J=8.8 Hz, 1H), 7.77 (d, J=2.0 Hz, 1H), 7.69 (dd, J=6.0 and 2.4 Hz, 1H), 7.30 (d, J=2.8 Hz, 1H), 7.03 (dd, J=6.0 and 2.4 Hz, 1H), 6.69 (d, J=8.4 Hz, 1H), 3.86 (s, 5H), 2.22 (s, 3H); $^{13}$C NMR (CDCl$_3$, 100 MHz) δ166.4, 157.2, 148.7, 147.2, 135.8, 129.4, 126.6, 124.0, 122.9, 122.2, 115.0, 114.6, 104.3, 55.8, 17.2; HRMS (ESI, m/z) for C$_{15}$H$_{15}$N$_2$OS calcd 271.0905, found 271.0906; Anal. calcd for C$_{15}$H$_{14}$N$_2$OS: C, 66.64; H, 5.22; N, 10.36. Found C, 66.68; H, 5.38; N, 10.48.

2-(4-Amino-3-methylphenyl)-6-trifluoromethylbenzothiazole (6j). yellow solid; 91% yield; mp 152-154; $^1$H NMR (CDCl$_3$, 400 MHz) δ8.12 (s, 1H), 8.04 (d, J=8.8 Hz, 1H), 7.83 (d, J=1.2 Hz, 1H), 7.77 (dd, J=6.0 and 2.4 Hz, 1H), 7.66 (dd, J=6.8 and 1.6 Hz, 1H), 6.72 (d, J=8 Hz, 1H), 4.20 (bs, NH$_2$), 2.24 (s, 3H); $^{13}$C NMR (CDCl$_3$, 100 MHz) δ171.1, 156.3, 148.3, 134.6, 130.0, 127.3, 126.4 (q, J=65.5 Hz, 1C), 123.0 (q, J=5.6 Hz, 1C), 122.4, 122.1, 118.9 (q, J=5.6 Hz, 1C), 114.5, 17.2; HRMS (ESI, m/z) for C$_{15}$H$_{12}$F$_3$N$_2$S calcd 308.0595, found 308.0597; Anal. calcd for C$_{15}$H$_{11}$F$_3$N$_2$S: C, 58.43; H, 3.60; N, 9.09. Found C, 58.50; H, 3.60; N, 9.09.

Cell Culture

Fibroblasts were obtained from adult foreskin specimens as previously described (Yang, C. C.; Lin, S. D.; Yu, H. S. *J. Dermatol. Sci.* 1997, 14, 162) and human basal cell carcinoma (BCC), purchased from American Type Culture Collection (Manassas, Va.), was maintained in RPMI1640 medium supplemented with 10% FCS and 100 U/mL penicillin G, and 100 μg/mL streptomycin sulfate (Gibco, BRL). BCC cells were passaged at confluence after treatment with 5 mM EDTA (Gibco, BRL) and incubated at 37 in a humidified atmosphere containing 5% CO$_2$.

UVA Irradiation

The method for UVA irradiation was described in the previous study (Kao, C. S.; Yu, H. S. *J. Invest. Dermatol.* 1992, 98, 734). For UVA irradiation, a specific UVA lamp emitting a peak wavelength of 365 nm with intensity of 0.75 mW/cm$^2$ (Vilber Lourmat, Moune La Vallee, Cedex, France) was used. The cultured cells were pretreated with different agents at 4 μM or pretreated with various concentrations (0-4 μM) of Formula 6 for 4 h before UVA irradiation. The cultured cells were rinsed with phosphate-buffered saline (PBS) and then irradiated with 1 J/cm$^2$ UVA in PBS to avoid the formation of medium-derived toxic photoproducts induced by UV exposure. The doses of irradiation were measured using a UVX radiometer (UVP, San Gabriel, Calif., USA) Immediately after phototreatment, PBS was removed and media were added to the cells. All the following experiments were performed three times in triplicate.

Cell Viability

Cell viability was assessed by the MTT assay, a mitochondrial function assay based on the ability of viable cells to reduce the redox indicator MTT to insoluble formazan crystals by mitochondrial dehydrogenase. Briefly, cells were seeded in a 96-well plate at the cell density of 2500 cells/well. After an overnight incubation, the cells were treated with compounds at 4 μM and incubated for 24 h. The medium was then discarded and replaced with 10 μL of MTT dye. Plates were incubated at 37° C. for 2 h. The resulting formazan crystals were solubilized in 100 μL DMSO, and the optical density was read at 540 nm with a microplate reader (MRX-II, Dynex technology, Chantilly, Va.).

Sub-G1 Region Analysis

BCC cells were treated with compounds at 4 μM and 1 J/cm$^2$ UVA. Twenty-four hours after irradiation, cells were harvested by trypsinization and centrifugation. Cell pellets were resuspended in 50% cold ethanol and fixed at −20° C. After fixation, cells were washed once with cold PBS and incubated in 0.5 mL of PBS containing 100 μg/mL RNase A for 20 min at 37° C. Cells were harvested by centrifugation at 400 g for 5 min, and 250 μL of PBS containing 50 μg/mL propidium iodide (PI) was added to the pellet. Thirty minutes later, the DNA contents of 10,000 events were measured by FACSscan flow cytometer (Elite ESP, Beckman Coulter, Brea, Calif.). Histograms were analyzed using Windows Multiple Document Interface software (WinMDI). Cells with DNA content less than that in untreated cells in G0/G1 were considered apoptotic.

Caspase-3 Colorimetric Assay

Twenty-four hours after irradiation, cells were collected by centrifugation, washed once with PBS, and cell pellets were counted and resuspended in 25 μL/1×10$^6$ cells of cold lysis buffer and homogenized. Homogenates were centrifuged at 12,000 rpm for 10 min at 4° C., supernatants were used for measuring caspase-3 activity using an ELISA-based assay, according to the manufacturer's instructions. (R&D Systems, Minneapolis, Minn.). The results were presented as mean±SD.

Annexin V and PI Binding Assay

To assess the simultaneous observation of early phase of apoptotic and necrotic features, BCC cells were treated with various concentrations (0-4 μM) of Formula 6f for 4 h before irradiation. Twenty-four hours after irradiation, cells were harvested by trypsinization and centrifugation and measured by cytometry by adding annexin V-FITC to 106 cells per sample according to the manufacturer's specifications (Bender MedSystems, Vienna, Austria). Simultaneously, the cells were stained with PI. Flow cytometry data were analyzed by the WinMDI software.

Morphology Observation

BCC or fibroblasts (5×10$^5$ cells/well) seeded on 6 well plate. Cells were treated with 4 μM Formula 6f for 4 h followed by 1 J/cm2 UVA irradiation. Twenty four hours after exposure, photos were taken by using microscope at 200× phase.

Determination of Intracellular ROS Level

To evaluate intracellular reactive oxygen species (ROS) levels, 2',7'-dichlorofluorescein diacetate (DCFH-DA, Molecular Probes) fluorescent dye was used to clarify this issue. The nonpolar DCFH-DA is converted to the polar derivative DCFH by esterases when it is taken up by the cell. DCFH is nonfluorescent but is rapidly oxidized to the highly fluorescent DCF by intracellular H2O2 or nitric oxide. In addition, catalase (Sigma), an effective H2O2 scavenger, was also used in this study. Cells were pretreated with catalase (800 U/mL) before Formula 6f (0-4 μM) treatment. After indicated irradiation, DCFH-DA (10 μM) was immediately added into cultured cells for 30 min at 37. The fluorescence of the samples was measured with a flow cytometer. The 2',7'-dichlorofluorescein (DCF) data were recorded using FL-1 photo multiplier.

Assessment of Mitochondrial Membrane Potential ($\Delta\Psi_{mt}$)

BCC cells were cultured in 35-mm dishes and allowed to reach exponential growth for 24 h before treatment. Cells were pretreated with 0, 2, and 4 M Formula 6f for 4 h before 1 J/cm$^2$ UVA irradiation. The medium was removed and the adherent cells trypsinized The cells were pelleted by centrifugation at 400 g for 5 min and stained in a 100 nM/ml DiOC$_6$ dye (Molecular Probes, Eugene, Oreg.) for 30 min at room temperature and washed with PBS twice and resuspended in PBS. The samples were analyzed immediately for fluorescence (FL-1 detector, filter 530/30 nm band pass) on a FAC-Scan flow cytometer (Elite ESP, Beckman Coulter, Brea, Calif.). Histograms were analyzed using Windows Multiple Document interface software (WinMDI).

ATP Content Bioluminescence Assay

The amount of intracellular ATP was determined by bioluminescent assay based on the measurement of the light output of the luciferin-luciferase reaction. After treatment with various concentrations of 6f-UVA, total cell extracts from cultured BCC cells were obtained immediately by lysing solution. After centrifugation to remove cell debris, the supernatants were collected for ATP measurement. The total amount of intracellular ATP was determined according to the protocol provided with the ATPLite assay kit (Perkin Elmer, Boston, Mass.).

Protein Extraction and Western Blot Analysis

Total cell extracts from cultured BCC cells were obtained by lysing the cells in ice-cold RIPA buffer (1×PBS, 1% NP-40, 0.5% sodium deoxycholate, 0.1% SDS) containing 100 μg/mL PMSF, 2 μg/mL aprotinin, 2 μg/mL leupeptin and 100 μg/mL NaF. After centrifugation at 14,000 g for 30 min, protein in the supernatants was quantified by Bradford method (Bio-Rad). Forty micrograms of protein per lane was applied in 10% SDS-poly-acrylamide gel. After electrophoresis, protein was transferred from the gel to polyvinylidene difluoride (PVDF) membrane (Millipore, Bedford, Mass.). The membranes were blocked at room temperature for 1 h in PBS+0.1% Tween 20 (PBS-T) containing 5% skim milk. After being briefly rinsed with PBS-T, the blots were probed with respective primary antibodies at room temperature for 2 h or at 4° C. overnight. Rabbit polyclonal antibodies against JNK (46 kDa), p38 (38 kDa), ERK (42, 44 kDa), and mouse monoclonal antibody against p-JNK, p-p38, p-ERK were purchased from Santa Cruz Biotechnology (Santa Cruz, Calif.). Mouse monoclonal antibody against actin was purchased from Chemicon Int. Inc. (Temecula, Calif.). For the blocking test, 25 μM oligomycin (Sigma, a mitochondria-specific $F_0F_1$ ATP synthase inhibitor) or 1×10$^{-4}$M ATP (Sigma) was added to the media 30 min before treated with 6f-UVA, respectively. The membrane was incubated with the corresponding horseradish peroxidase-labeled secondary antibody (Santa Cruz Biotechnology) at room temperature for 1 h. Membranes were washed with PBS-T four times for 15 min, and the protein blots were visualized with Western Lightning Chemiluminescence Reagent Plus (Perkin Elmer Life Sciences, Boston, Mass.). The relative amounts of specific proteins were quantified by densitometry scanning of X-ray films and analyzed by Eagle Eye Image System (Stratagene, La Jolla, Calif.)

Statistical Analysis

The results were expressed as means±SD and analyzed by using the statistical analysis system (SPSS, SPSS Inc., Chicago, Ill.). Differences among groups were analyzed by Student's t-test. P values <0.05 were considered as significant for all statistical tests.

Example 2

Results

Cell Viability

Figure 3A:
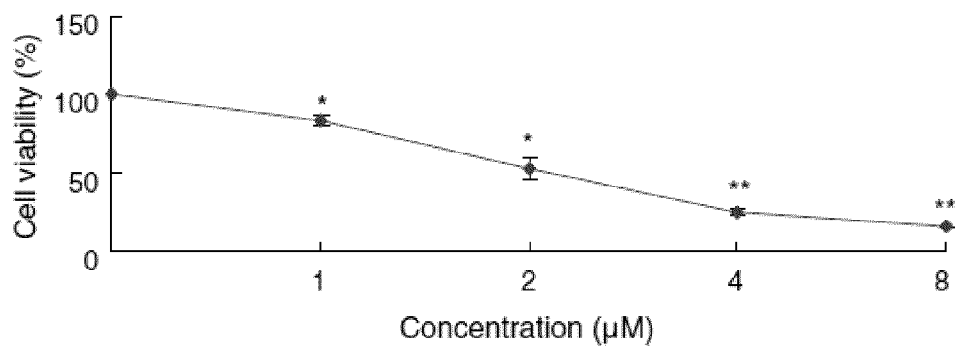
FIG. 3 shows effect of 6-UVA cell viability. (A) Dose-response curves for compound 6 f tested against BCC cells. Cells were seeded in a 96-well plate at 2500 cells per well and cultivated overnight until cell attachment. 6f-UVA at the indicated concentration was added into the culture media in triplicate and incubated for 4 h before 1 J/cm2 UVA irradiation. Twenty-four hours after irradiation, the MTT reagent was added into each well. The absorbance is directly proportional to the number of living cells. (B) To clarify whether 6-UVA has more cytotoxicity than either UVA irradiation alone or treatment with 6 alone, cells were cultured with or without 4 μM Formula 6f before different dosage of UVA irradiation. $*p<0.05$, $**p<0.01$ as compared with the control.
Figure 3B:
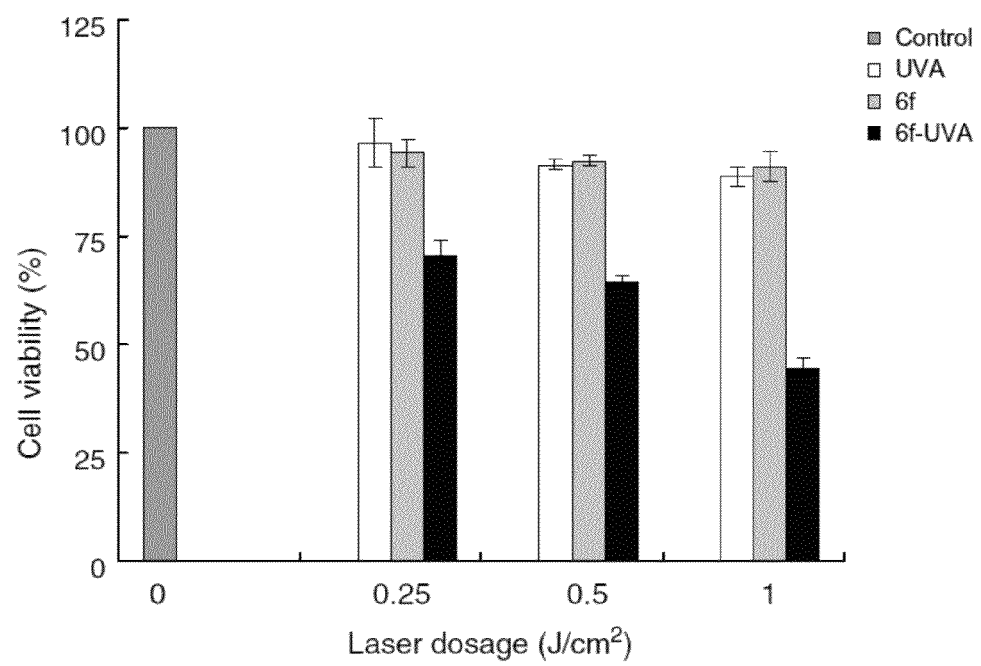

The effect of UVA-activated Formula 6 on BCC cell viability was evaluated by MTT assay. BCC cells were treated with different concentrations of Formula 6f (i.e. Formula 6 wherein R$_1$ was 6-CF$_3$ and R$_2$ was H) for 4 h followed by 1 J/cm$^2$ UVA irradiation. Twenty-four hours after exposure, cell viability was determined As shown in FIG. 3A, the inhibitory effect is dependent on drug concentration. At concentrations of 4 μM Formula 6f, the cell survival was below 50% after 1 J/cm$^2$ UVA irradiation. To elucidate whether 1 J/cm$^2$ UVA irradiation is the most effective dosage in this study, cells were pretreated with 4 μM Formula 6f before UVA treatment. Compared with that of the untreated controls, the cell viability of BCC cells was 71, 65, and 45% after irradiation with 0.25, 0.5, and 1 J/cm$^2$ UVA treatment respectively. In addition, the data also showed that 6-UVA exhibited a higher inhibitory activity more than either UVA irradiation alone or treatment with exogenous Formula 6 alone, and Formula 6f alone does not have cytotoxicity against BCC cells (FIG. 3B).

Cellular Sub-G1 Accumulation

To investigate the effects of compounds 6 on cell cycle progression of BCC cells, the DNA content of cell nuclei was measured by flow cytometric analysis. Agent action resulted in cells having a hypodiploid DNA content (sub-G1 material) that is characteristic of apoptosis and reflects fragmented DNA. BCC cells were treated with 4 µM agents for 4 hours followed by 1 J/cm$^2$ UVA irradiation. Twenty-four hours after irradiation, the PI reagent was used. Approximately 10000 cells from each group were analyzed with the FACScan flow cytometer. The apoptotic effects in 2.2% (control), 6.5% (6a), 13.4% (6b), 29.2% (6c), 24.4% (6d), 6.5% (6e), 35.4% (6f), 13.6% (6g), 13.8% (6h), 14.8% (6i) and 6.4% (6j) of sub-G1 DNA peak were obtained (% represented the percentage of cell counts). Because the compound of Formula 6f exhibited the most sub-G1 accumulation on BCC cells, it was selected as a model for further studies.

Apoptosis Detection

Figure 4A:
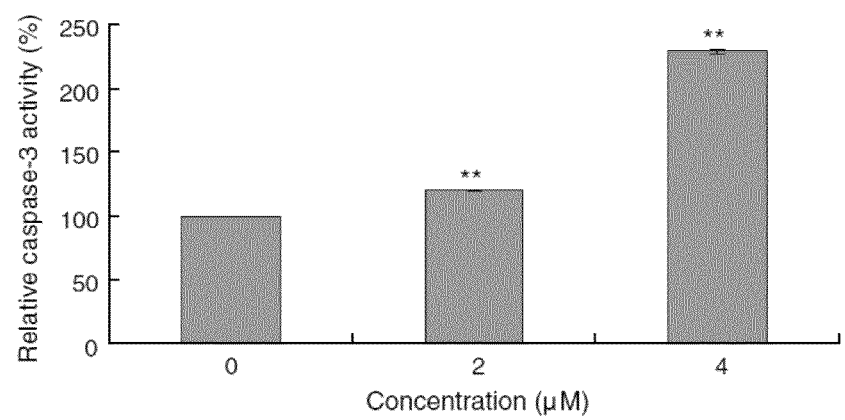
FIG. 4 shows effect of 6f-UVA treatment on cell apoptosis. (A) The increased enzymatic activities of the caspase-3 in apoptotic were determined by colorimetric reaction. The cleavage of peptide by the caspase releases the chromophore pNA (p-nitroaniline), which can be quantified spectrophotometrically at a wavelength of 405 nm (B) Dot plots for BCC cells treated with various concentrations of 6f-UVA and then stained with PI and an annexin V-FITC conjugate specifically detecting the exposure of PS residues at the cell surface. (C) Morphological observation and annexin V/PI double stain were used for the detection of fibroblasts apoptosis. Approximately 10000 cells from each group were analyzed by flow cytometry. Data shown are of a representative experiment repeated three times with similar results. ** $p<0.01$ as compared with the control.
Figure 4B:
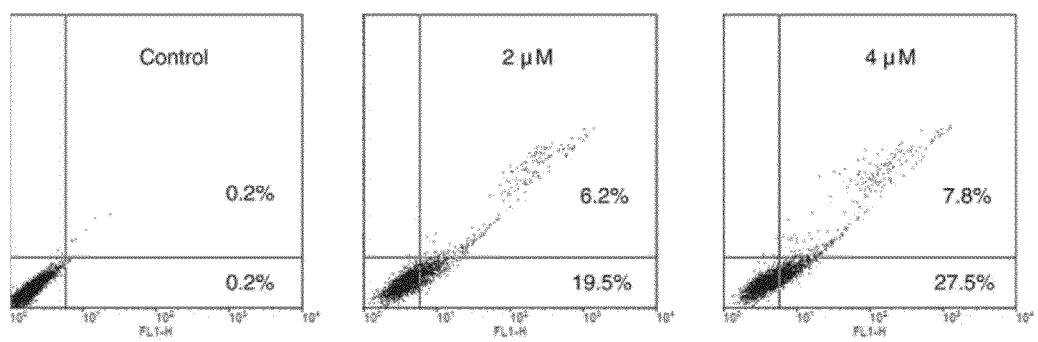
Figure 4C:
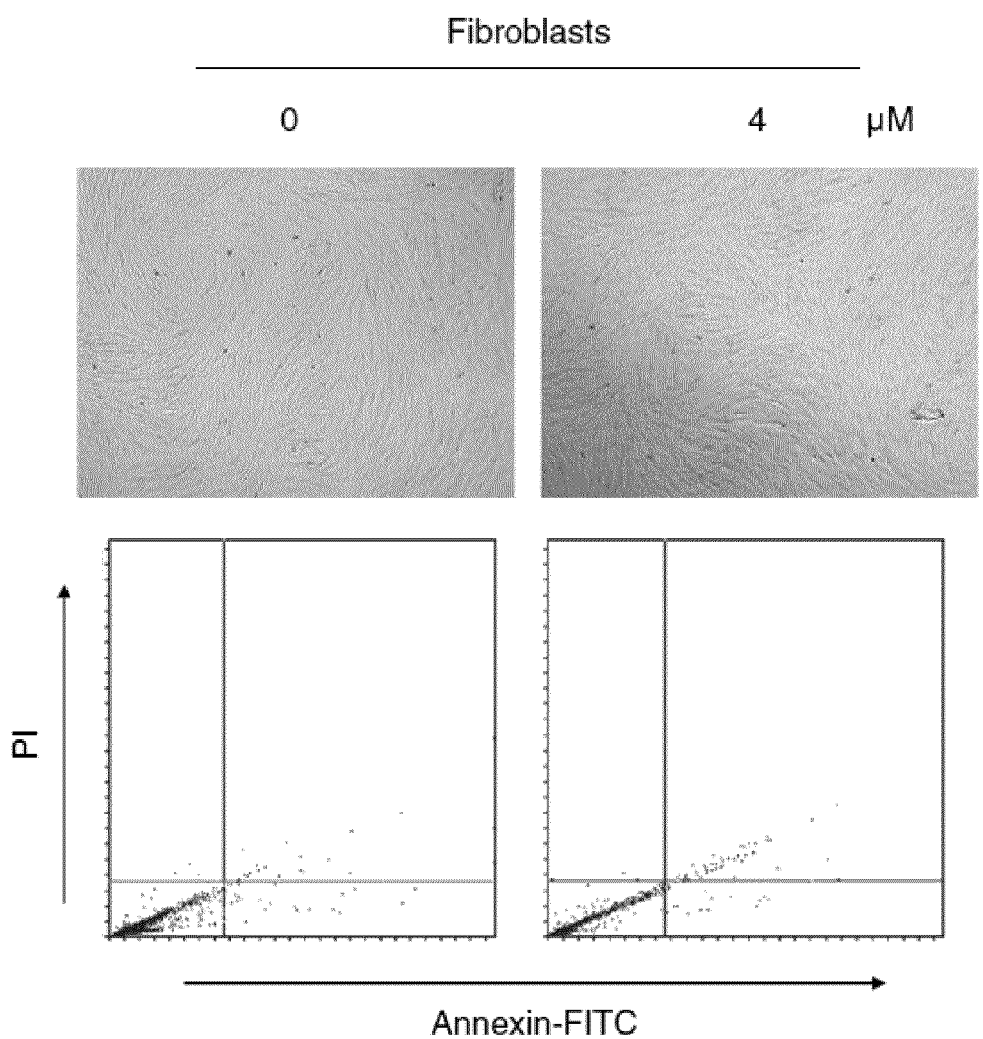

Caspase-3 had been shown to be one of the most important cell executioners for apoptosis (Shi, Y. *Mol. Cell* 2002, 9, 459). The expressions of caspase-3 activity were determined using colorimetric assay. Compared with the untreated control group, the caspase-3 activity of BCCs increased after 6f-UVA treatment ($p<0.01$) (FIG. 4A). Moreover, treatment of BCC cells with 0, 2, and 4 µM Formula 6f at 1 J/cm$^2$ UVA irradiation induced apoptotic cells (annexin V$^+$/PI$^-$) at levels of 0.2%, 19.5%, and 27.5% respectively. In contrast, there was no obvious change of necrotic cells (annexin V$^+$/PI$^-$) (FIG. 4B). In addition, it would be interesting to know the apoptotic activity of 6f-UVA on normal cells. Thus, human dermal fibroblast cells were used to clarify this issue. Data from morphology observation and annexin V/PI binding assays showed that no significant apoptotic effect was seen after 6f-UVA treatment as compared with the control group (FIG. 4C). These results encouraged the further study of the apoptotic mechanism involved in photosensitive effects induced by 6f-UVA in BCC cells.

Mitochondrial Dysfunction

Figure 5A:
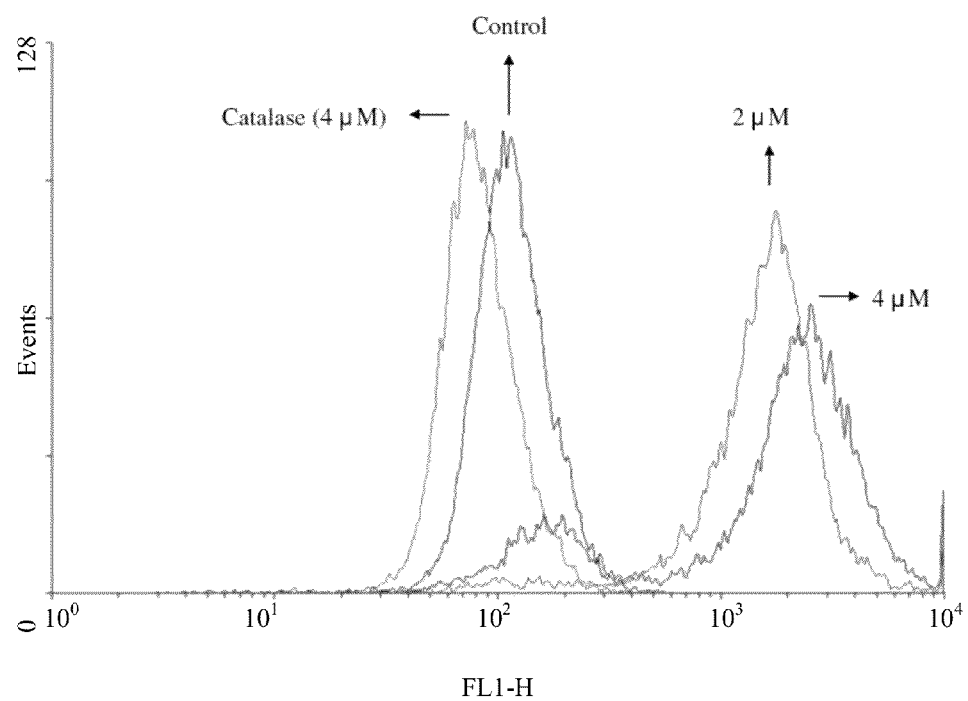
FIG. 5 shows effect of 6f-UVA on the mitochondrial function. (A) 6f-UVA induced ROS generation in BCC cells. Histogram of fluorescence vs cell count in BCC cells with various concentrations of 6f-UVA and stained with DCFH-DA. As a control, ROS was measured in the presence of catalase, a $H_2O_2$ scavenger. (B) The $\Delta\Psi_{mt}$ of BCC cells after exposure to 6f-UVA. Cells were treated with 0, 2, and 4 μM Formula 6f for 4 h followed by 1 J/cm2 UVA irradiation, then stained with $DiOC_6$ and analyzed immediately by flow cytometry as described under Materials and Methods. The number in M1 indicates the percentage of cells with reduced $\Delta\Psi_{mt}$. Approximately 10000 cells from each group were analyzed by flow cytometry. (C) Relative ATP levels were calculated as the percentage of the 0 μM level. Similar results were obtained in three independent experiments. *p<0.05, ** p<0.01 as compared with the control.
Figure 5B:
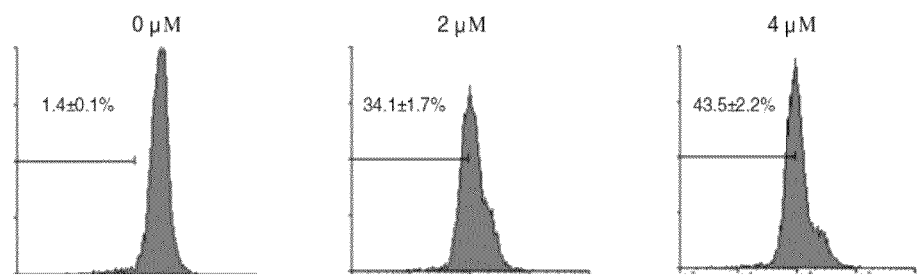
Figure 5C:
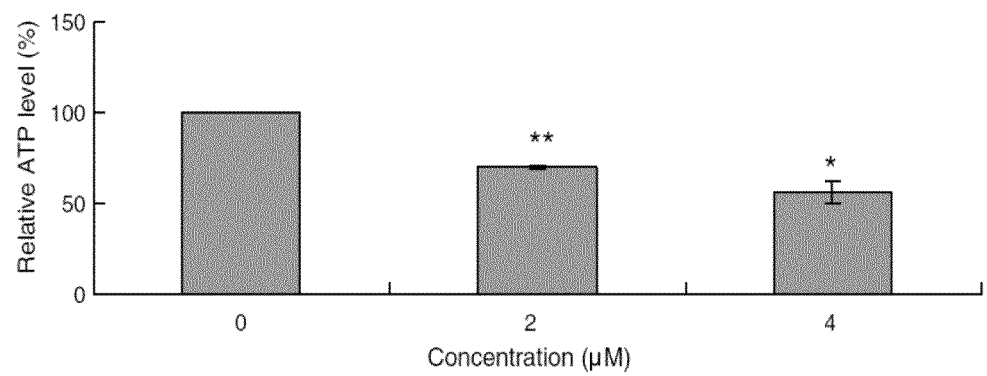

Growing evidence suggested that mitochondrial dysfunction plays a key role in oxidative stress (Hail, N. Jr. *Apoptosis* 2005, 10, 687), which induces production of ROS, and can lead to the apoptotic mode of cell death. To determine whether ROS was involved in 6f-UVA-induced mitochondria dependent apoptosis, the production of intracellular $H_2O_2$ was measured by using the DCFH-DA probe. The result showed that 6f-UVA significantly increased intracellular $H_2O_2$ levels. In addition, catalase significantly abrogated the increased ROS production of BCC cells treated with 4 µM 6f-UVA (FIG. 5A). Mitochondrial membrane potential ($\Delta\Psi_{mt}$) is an important parameter not only for mitochondrial but also cellular status. A decline of $\Delta\Psi_{mt}$ is an early event in the process of cell death. The decrease of fluorescence intensity reflects the collapse of $\Delta\Psi_{mt}$, which generally defined an early but already irreversible stage of apoptosis. Therefore, the present invention examined whether the initial ROS generation after 6f-UVA altered $\Delta\Psi_{mt}$. BCC cells were harvested after 0, 2, and 4 µM 6f-UVA treatment, then analyzed by flow cytometry after DiOC$_6$ dye labeling. The dye binds to the inner and outer membrane of mitochondria and undergoes a red shift in fluorescence during membrane depolarization. As demonstrated in FIG. 5B, cells treated with dosages equal to or greater than 2 µM exhibited significant decline of $\Delta\Psi_{mt}$ in BCC cells. ATP was the central parameter of cellular energetics, metabolic regulation and cellular signaling; therefore, determination of intracellular ATP is worthwhile in the characterization of cellular physiology. Compared with that of untreated control, the intracellular ATP content of BCC cells decreased about 30% and 45% after 2, and 4 µM of 6f-UVA treatment respectively (FIG. 5C).

Activation of MAPKs Pathways

Figure 6A:
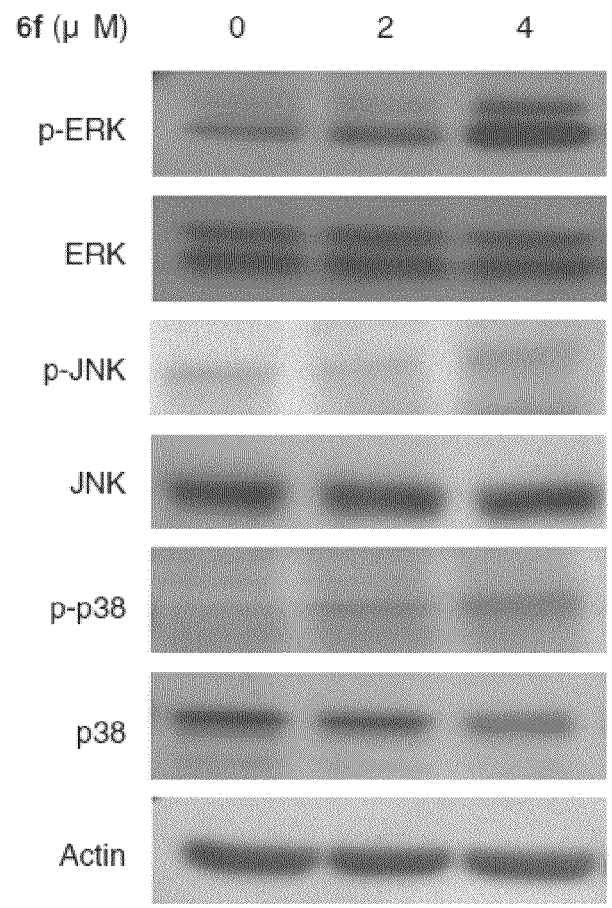
FIG. 6 shows the immunoblot analysis which showed the effect of 6f-UVA on the protein expression of MAP kinases on BCC cells. (A) After exposure to different concentration of 6f-UVA, cell lysates were collected and immunoblotted with specific antibodies as indicated. For the internal control, the same amounts of protein extract were also probed with antibody against actin. (B) As a control, the expression level of p-ERK was determined in the presence of oligomycin (25 μM) and ATP (1×10$^{-4}$M)
Figure 6B:
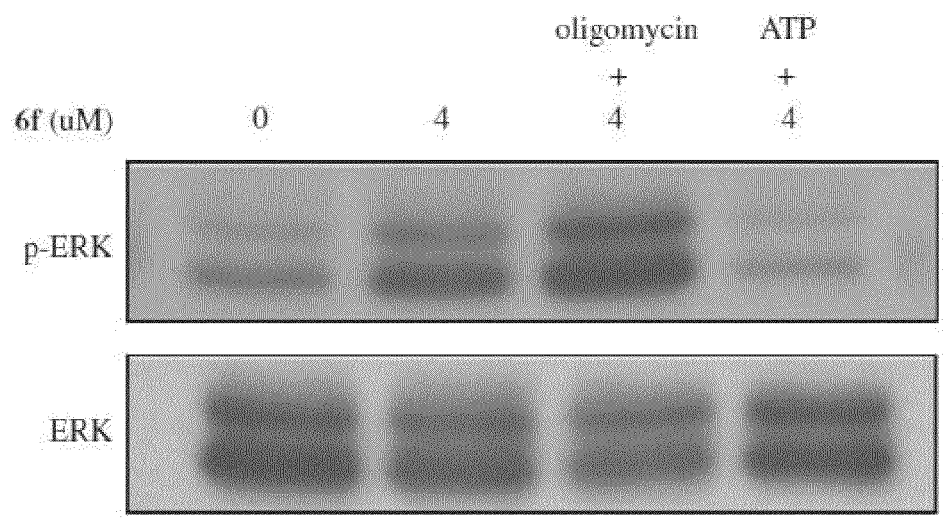

To determine the potential involvement of various protein kinase pathways in 6f-UVA-induced apoptosis, MAPK activities were evaluated by measuring phosphorylation of MAPK subfamilies Compared with the untreated control group, the phosphorylation of ERK (p-ERK) and p38 (p-p38) of BCC cells increased after treatment with 6f-UVA at a concentration of 4 µM. In contrast to ERK and p38, treatment of BCC cells with 6f-UVA did not stimulate the phosphorylation of JNK MAPK (FIG. 6A). Moreover, to elucidate whether the activity of MAPK might be due to the decrease in cellular ATP synthesis, cells were pretreated with oligomycin (a mitochondria-specific $F_0F_1$ ATP synthase inhibitor) or ATP before 4 µM 6f-UVA treatment. The results showed that pretreatment with oligomycin but not ATP increased the ERK activation (FIG. 6B)

One skilled in the art readily appreciates that the present invention is well adapted to carry out the objects and obtain the ends and advantages mentioned, as well as those inherent therein. The compounds, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of providing photodynamic therapy to a patient having at least one tumor comprising the steps of: administering the compound of formula 6

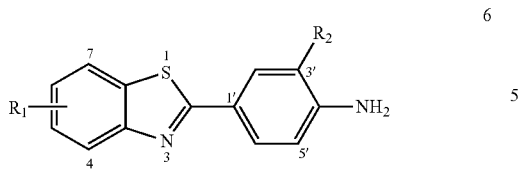

6 in a pharmaceutically acceptable carrier to the patient; waiting for a sufficient time to allow the administered compound to be taken up by a target tissue having the at least one tumor; and irradiating a region of the patient containing the target tissue, wherein growth of the tumor is inhibited; wherein R1 of formula 6 is $C_{1-10}$ haloalkyl, and R2 of formula 6 is H or $C_{1-10}$ alkyl.

2. The method of claim 1, wherein the patient has skin cancer.

3. The method of claim 2, wherein the patient has basal cell carcinoma.

4. The method of claim 1, wherein the compound of formula 6 is activated by UVA.

5. The method of claim 1, wherein the growth of the tumor is inhibited by apoptosis of tumor cells.

6. The method of claim 5, wherein intracellular $H_2O_2$ levels in the tumor cells are increased.

7. The method of claim 5, wherein intracellular mitochondrial membrane potential ($\Delta\Psi_{mt}$) in the tumor cells is declined.

* * * * *